United States Patent
Szoka

(10) Patent No.: US 11,389,266 B2
(45) Date of Patent: Jul. 19, 2022

(54) SURGICAL DEVICES AND METHODS FOR BARIATRIC AND GASTROESOPHAGEAL SURGERY

(71) Applicant: West Virginia University Board of Governors on behalf of West Virginia University, Morgantown, WV (US)

(72) Inventor: Nova Szoka, Morgantown, WV (US)

(73) Assignee: West Virginia University Board of Governors on behalf of West Virginia University, Morgantown, WV (US)

( * ) Notice: Subject to any disclaimer, the term of this patent is extended or adjusted under 35 U.S.C. 154(b) by 0 days.

(21) Appl. No.: 17/590,567

(22) Filed: Feb. 1, 2022

(65) Prior Publication Data

US 2022/0151724 A1    May 19, 2022

Related U.S. Application Data

(63) Continuation of application No. 16/836,396, filed on Mar. 31, 2020.
(Continued)

(51) Int. Cl.
*A61B 90/30* (2016.01)
*A61B 1/00* (2006.01)
(Continued)

(52) U.S. Cl.
CPC .......... *A61B 90/30* (2016.02); *A61B 1/00066* (2013.01); *A61B 1/00078* (2013.01); *A61B 1/00105* (2013.01); *A61B 1/0669* (2013.01); *A61B 1/0684* (2013.01); *A61B 1/2736* (2013.01); *A61B 1/303* (2013.01);
(Continued)

(58) Field of Classification Search
CPC .......... A61B 90/30; A61B 17/24; A61B 90/06
See application file for complete search history.

(56) References Cited

U.S. PATENT DOCUMENTS 5,423,321 A    6/1995 Fontenot
5,624,432 A    4/1997 Angelchik
(Continued)

FOREIGN PATENT DOCUMENTS

CN    2551172 Y    5/2003
WO    2017011085 A1    1/2017
(Continued)

OTHER PUBLICATIONS

Nandra, K. and Ing, R. Safety of Orogastric Tubes in Foregut and Bariatric surgery. Surgical Endoscopy. 2018, 3 pages.
(Continued)

*Primary Examiner* — Andrew Yang
(74) *Attorney, Agent, or Firm* — Morgan Lewis & Bockius LLP

(57) ABSTRACT

Disclosed are various embodiments for improved surgical devices and methods of using the same in connection with bariatric and gastroesophageal surgery. The present disclosure includes a lighted bougie device that can include an elongate member and a light source. The light source can be configured to emit near-infrared light. The light source can also be positioned about the bougie such that light emitted from the light source illuminates along a portion of the bougie.

21 Claims, 9 Drawing Sheets
(2 of 9 Drawing Sheet(s) Filed in Color)

Related U.S. Application Data

(60) Provisional application No. 62/827,359, filed on Apr. 1, 2019.

(51) Int. Cl.

| | | |
|---|---|---|
| *A61B 1/31* | (2006.01) | |
| *A61B 1/307* | (2006.01) | |
| *A61B 1/303* | (2006.01) | |
| *A61B 1/32* | (2006.01) | |
| *A61B 1/273* | (2006.01) | |
| *A61B 90/00* | (2016.01) | |
| *A61F 5/00* | (2006.01) | |
| *A61B 1/313* | (2006.01) | |
| *A61B 34/30* | (2016.01) | |
| *A61B 1/06* | (2006.01) | |
| *A61M 1/00* | (2006.01) | |
| *A61B 17/00* | (2006.01) | |
| *A61M 25/00* | (2006.01) | |

(52) U.S. Cl.
CPC ............. *A61B 1/307* (2013.01); *A61B 1/31* (2013.01); *A61B 1/3132* (2013.01); *A61B 1/32* (2013.01); *A61B 34/30* (2016.02); *A61B 90/361* (2016.02); *A61F 5/0076* (2013.01); *A61F 5/0086* (2013.01); *A61F 5/0089* (2013.01); *A61M 1/741* (2021.05); *A61M 1/84* (2021.05); *A61B 2017/00725* (2013.01); *A61B 2090/304* (2016.02); *A61B 2090/306* (2016.02); *A61B 2090/309* (2016.02); *A61B 2090/3979* (2016.02); *A61M 25/007* (2013.01)

(56) References Cited

U.S. PATENT DOCUMENTS

| | | | |
|---|---|---|---|
| 5,879,306 A | 3/1999 | Fontenot et al. | |
| 6,185,356 B1* | 2/2001 | Parker | A61B 17/02 362/559 |
| 9,375,137 B2 | 6/2016 | Sherwinter | |
| 9,603,735 B2 | 3/2017 | Trivedi | |
| 9,808,368 B2 | 11/2017 | Radl et al. | |
| 9,999,533 B2 | 6/2018 | Radl et al. | |
| 10,182,933 B2 | 1/2019 | Rokde et al. | |
| 2005/0203500 A1 | 9/2005 | Saadat et al. | |
| 2015/0164310 A1* | 6/2015 | Holt | A61M 16/0486 128/207.29 |
| 2015/0290414 A1* | 10/2015 | Vasan | A61B 1/00032 128/200.26 |
| 2016/0250056 A1* | 9/2016 | Keren | A61B 17/064 606/144 |
| 2018/0008156 A1 | 1/2018 | Pandolfino et al. | |
| 2019/0388635 A1* | 12/2019 | Loewen | A61B 1/0669 |

FOREIGN PATENT DOCUMENTS

| | | |
|---|---|---|
| WO | 2018152427 A1 | 8/2018 |
| WO | 2020095135 A1 | 5/2020 |

OTHER PUBLICATIONS

Frantzides, CT, et al. Laparoscopic Transgastric Esophageal Mucosal Resection for High-Grade Dysplasia. Journal of Laparoendoscopic & Advanced Surgical Techniques. 2004. 14:5, 5 pages.

Dobruskin, L, et al. Infrared Illumination During Thoracoscopic Excision of Mediastinal Bronchogenic Cysts. Journal of Laparoendoscopic & Advanced Surgical Techniques. 2005. 15:1, 3 pages.

Diversatek, Inc., Diversatek Healthcare, InnerVision Transillumination System Brochure 2017, 4 pages.

"Evaluation of the ViSiGiTM Calibration System" ClinicalTrials. gov, Dec. 11, 2013, via the internet <https://clinicaltrials.gov/ct2/show/record/NCT02008825?view=record>.

"Class 2 Device Recall Stryker Infravision Esophageal Kit", U.S Food & Drug Administration, dated Dec. 28, 2010, via the internet <https://www.accessdata.fda.gov/scripts/cdrh/cfdocs/cfres/res.cfm?id=84866>.

* cited by examiner

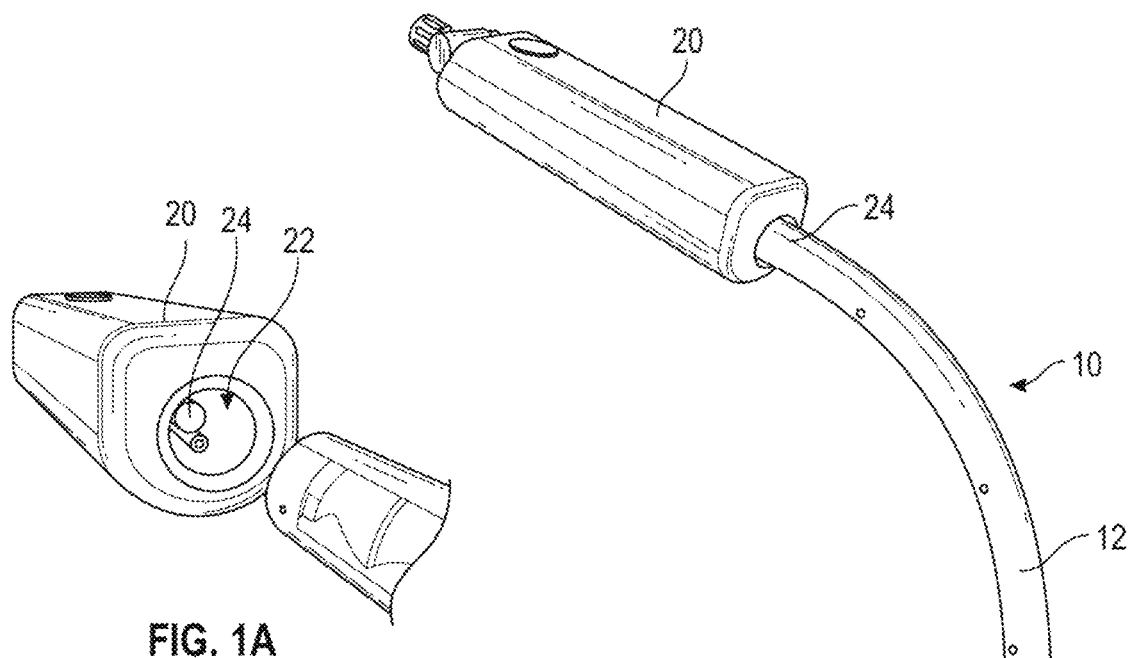
FIG. 1A
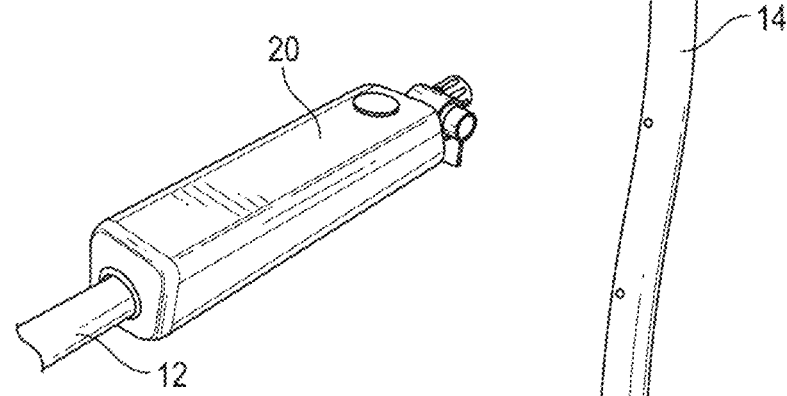
FIG. 1B
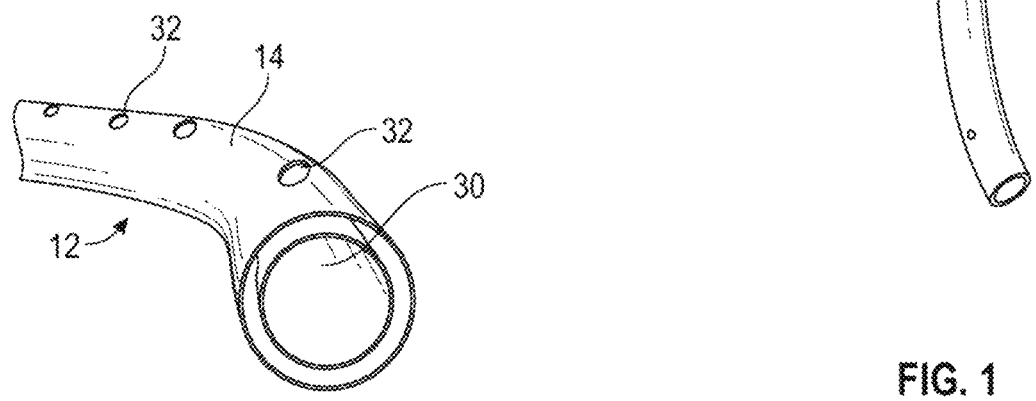
FIG. 1C
FIG. 1

Figure I (a) Passing lighted Bougie in white light.

Figure I (b) Passing lighted Bougie in near infrared light.

Figure II (a) Passing lighted Bougie (endoscope) in white light.

Figure II (b) Passing lighted Bougie (endoscope) in near infrared light, proximal stomach.

SURGICAL DEVICES AND METHODS FOR BARIATRIC AND GASTROESOPHAGEAL SURGERY

CROSS-REFERENCE TO RELATED APPLICATIONS

This application is a continuation application of U.S. Patent Application No. 16/836,396 filed Mar. 31, 2020, which claims the benefit of and priority to co-pending U.S. Provisional Patent Application No. 62/827,359, filed on Apr. 1, 2019, entitled "USE OF NEAR-INFRARED CAMERA AND LIGHTED BOUGIE TO IMPROVE SLEEVE GASTRECTOMY TECHNIQUE," the contents of which is incorporated by reference herein in its entirety.

BACKGROUND

Obesity and its associated costs represent a significant healthcare issue in the United States and worldwide. Treatments for obesity vary from dietary and behavioral changes and increasing healthy exercise/activity, to prescription medications, and weight-loss surgery. Bariatric surgery has become the standard of care for treatment of severe obesity and obesity related health problems, due to its proven ability to achieve sustained weight reduction, as well as reduction of the comorbidities related to obesity. Scientific studies cite benefits such as weight loss, as well as high rates of improvement or resolution of diabetes, hyperlipidemia, hypertension, and obstructive sleep apnea after a bariatric procedure. Laparoscopic sleeve gastrectomy (LSG) has overtaken Roux en Y gastric bypass (RNY) as the most widely performed procedure in both community and academic practices.

The most common complications of sleeve gastrectomy and gastric bypass operations include leak (1%), bleeding, and venous thromboembolism. However, another complication of these operations is bougie-related injury. Bougie-related injury is defined as an injury to the patient that occurs as a result of bougie placement or use. Within the bariatric literature the incidence of bougie-related injury is 0.1-1.2%. Reported injuries most commonly occur in bariatric operations while stapling the gastric sleeve or gastric pouch. Comparatively, within the foregut surgical literature, the incidence of bougie-related injury is 0.8-1.6%, with most common injuries occurring while passing the bougie down the esophagus into the stomach which can cause either esophageal or gastric perforation. Based on the lower rate of bougie-related injury in the bariatric literature, there is concern that these injuries may currently be under-reported.

A bougie-related injury can occur during many different surgical procedures. Iatrogenic instrument-related injuries can include accidental stapling of tube, probe, or bougie during gastric sleeve or gastric pouch formation, as well as esophageal or gastric perforation from insertion of a bougie. For example, a bougie-related injury can occur in a bariatric surgery while advancing the bougie down the esophagus into the stomach, while creating a gastric sleeve during laparoscopic sleeve gastrectomy, or while creating the gastric pouch during laparoscopic gastric bypass. Typical bougie-related injuries can include, proximal, mid, or distal esophageal perforation; proximal, mid or distal gastric perforation, as well as stapling the bougie into the stomach, necessitating immediate revision/reconstruction, or stapling across the bougie and leaving a foreign body behind inside or outside the patient.

Furthermore, minimally invasive surgery, and especially robotic surgery, provides decreased tactile feedback to the surgeon, which is associated with increased risk of iatrogenic esophageal and gastric injury during bougie insertion, gastric sleeve formation, or gastric pouch formation. These types of injuries can result in serious morbidity and even mortality if they go undetected until after the procedure, and even when detected immediately, they can require lengthy and costly procedural modifications that result in increased morbidity and longer hospital stay. Therefore, laparoscopic visualization is necessary to ensure proper performance of the procedure. However, as a minimally invasive approach has become the gold standard in bariatric surgery, this has led to decreased tactile feedback and greater reliance on laparoscopic two-dimensional white light visualization. Furthermore, with the growing use of robotic bariatric surgery, where the surgeon is remote from the patient with even more limited tactile sensation, the need for additional safety techniques/tools to evaluate and perform minimally invasive surgical procedures is necessary.

Despite the large number of laparoscopic sleeve gastrectomies performed in the worldwide annually, there is no fully standardized technique for this operation. A consensus of experts agrees on the basic steps of the operation, namely to mobilize the stomach by dividing the short gastric arteries along the greater curvature, and to divide the stomach starting 6 cm from the pylorus, taking care not to narrow the stomach at the incisura or the angle of His. A bougie is passed to help maintain uniform sleeve size. However, within the bariatric community, there are still wide variations in terms of port placement, bougie size, when to pass a bougie, stapler length and size, as well as use of staple line reinforcement versus over-sewing the staple line.

White light is typically used to illuminate the abdominal cavity during laparoscopic procedures including bariatric and other gastroesophageal operations. Standard white light laparoscopic visualization illuminates the abdominal cavity and captures white light reflecting off the outside of the stomach and other organs. Near-Infrared cameras are now used in intra-abdominal procedures in conjunction with indocyanine green (ICG) dye to improve visualization of anatomy and tissue perfusion. White light cameras do not consistently show lighted instruments inside the stomach well if the stomach tissue is excessively thick. The near infrared camera demonstrates improved visualization of lighted instruments within the stomach—regardless of stomach tissue thickness.

Near infrared light has inherent transmissivity though biological tissues in the range of 700 nm to 1300 nm. All biological tissues are composite structures that can absorb specific wavelengths of light. The chemical and physical properties of different molecules in biologic tissue affect the amount and wavelengths of light that can be absorbed by the tissue. In the visible light spectrum (400-650 nm), intense light absorption of the hemoglobin molecule and light loss due to scattering prevents transmission of visible light more than a few millimeters of tissue. The entire near infrared spectrum is defined as light generally having wavelengths from 700-2500 nm. In the infrared spectrum above 1300 nm, water present in tissue absorbs a large amount of infrared light, thus limiting infrared light transmission through tissue to a short distance. In the near infrared range of 700 to 1300 nm, a significant portion of near infrared light can be transmitted though several centimeters of biological tissue. This window of high transmissivity is caused by the absence of molecules that absorb near infrared light between 700 nm and 1,300 nm. Embodiments of the present disclosure capitalize on the fact that this spectrum of near infrared energy can be transmitted through several centimeters of biological tissue and allow for transillumination of an organ during an invasive procedure.

BRIEF SUMMARY OF THE INVENTION

The lighted bougie device of the present disclosure can improve the consistency and reproducibility of construction of the gastric sleeve during sleeve gastrectomy, as well as the gastric pouch during gastric bypass. It can also improve intraoperative visualization for the surgeon and operative team to decrease the risk iatrogenic bougie related injury for the above bariatric operations, as well as other gastroesophageal operations, such as hiatal hernia repair, paraesophageal hiatal hernia repair, heller myotomy (in additions to other surgical procedures as discussed herein).

In one aspect the present disclosure includes example embodiments of a lighted bougie device that includes an elongate member and a light source. The light source is configured to emit near-infrared light. The light source is also positioned about the bougie such that light emitted from the light source illuminates along a portion of the bougie.

In another aspect the present disclosure includes example embodiments of an elongated member sized and shaped for placement around a surgical instrument. The elongated member also includes a lighting system disposed along an exterior surface of the elongated member and it is configured to illuminate along a length of the elongated member. Optionally, the surgical instrument is a bougie.

In another aspect the present disclosure includes methods of using various example embodiments of surgical instruments disclosed herein. An example method includes the step of inserting a bougie of a lighted bougie device into an esophagus and/or stomach of a patient. The method also the step of illuminating an operative field with a light emitted from a light source of the lighted bougie device and the step of determining a location of the bougie within the patient based on images captured from an image capturing device.

In still another aspect the present disclosure includes example embodiments of a lighted bougie device for use with a medical patient having an operative field. The lighted bougie device includes a bougie and at least one light source configured to emit near-infrared light. The light source is positioned about the bougie such that light emitted from the at least one light source illuminates substantially along a length of the bougie positioned within the operative field. The light source also includes spaced apart indicia that correlate to intervals of distance to allow for measuring with the operative field.

These and other aspects of the present disclosure will be discussed in more detail as set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is a perspective view of a lighted bougie device according to various embodiments of the present disclosure.

FIG. 1A-1C are close up views of various components of the lighted bougie device of FIG. 1.

DETAILED DESCRIPTION

Figure 2:
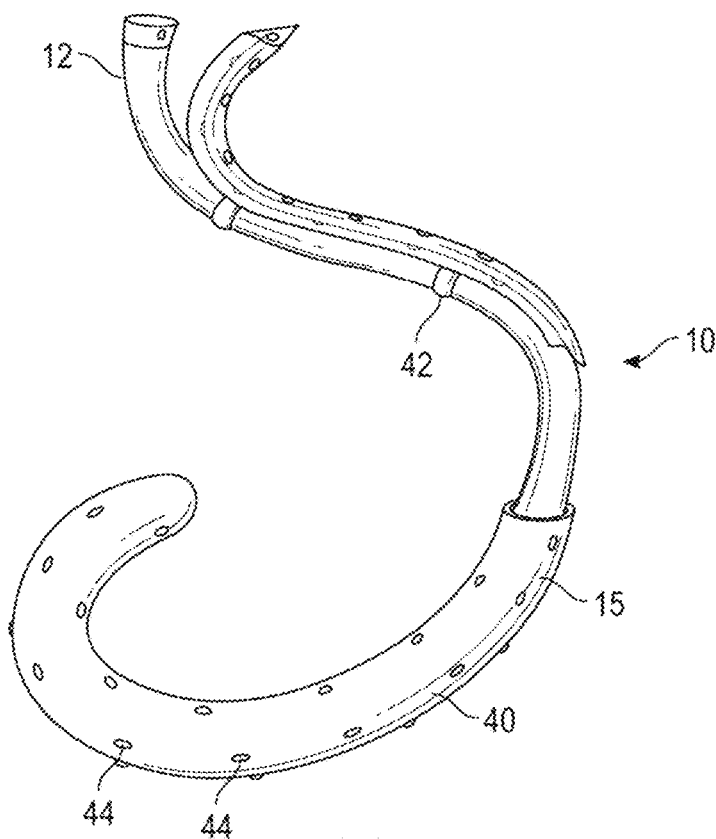
FIG. 2 is a perspective view of a lighted bougie sleeve device according to various embodiments of the present disclosure.

The present disclosure relates to a lighted bougie device for medical procedures. A bougie is a thin cylindrical device that a physician inserts into a body passageway, such as the esophagus or stomach, to diagnose or treat a condition. A bougie can be made of silicone, rubber, plastic, or any other suitable material. A bougie can be used in bariatric, thoracic, and foregut surgeries to ensure esophagogastric patency during specific portions of an operation. According to various embodiments, and among other purposes/uses as described herein, the lighted bougie device of the present disclosure is designed to (1) improve visualization while passing the bougie into the stomach during laparoscopic or robotic surgical procedures, which may lead to (2) decreased bougie-related injuries, (3) improve the ability of the surgeon in a bariatric operation to construct a consistent size of gastric sleeve or gastric pouch, as well as (4) improve overall team communication during said procedures.

With general reference, the lighted bougie device of the present disclosure comprises a light system coupled to an elongated cylindrical element. According to various embodiments, the light system can comprise an LED, fiber optic, or other lighting system. The light system can generate a white light or a near-infrared light that can be detected by a white light camera, as well as a near infrared camera. In example embodiments, the light system is positioned at a distal end of the elongated cylindrical element such that when the light system emits a light, the light is dispersed within the elongated cylindrical element and the light can illuminate an entire length of the same. When the near-infrared light is used in conjunction with a near-infrared camera during a laparoscopic procedure, the location of the bougie (e.g., elongated cylindrical element) within the esophagus can be determined regardless of the thickness of the tissue surrounding the bougie. This feature can improve visualization while passing the bougie into the stomach from the esophagus. Additionally, bougie-related injuries may be avoided by being able to have a better understanding of the location of the bougie during insertion. The lighted bougie device of the present disclosure can be used in conjunction with a camera that has white light and near infrared capabilities and can be used without the use of concurrent indocyanine green (ICG) dye.

For instance, FIGS. 1 and 1A-1C illustrate an example of the lighted bougie device 10 according to various embodiments of the present disclosure. Generally, the lighted bougie device 10 comprises an elongated cylindrical element 12 (e.g., a bougie) coupled to a handle 20. The handle can comprise a lighting device 22 that can provide light along the entire length of the attached cylindrical element (as better seen in FIG. 1A). The lighting device 22 can comprise an LED, fiber optic, or other light source, including near-infrared fluorescent polymers, 24 that is configured to generate white light and/or near-infrared light that can be detected by both a white light camera, as well as a near infrared camera. The light source can be directly adjacent to a distal end 24 of the cylindrical element 12 such that when the light source is activated, the light is transmitted through the interior of the cylindrical element.

The cylindrical element 12 can comprise one or more suctioning channels 30 extending along a length of the cylindrical element. The cylindrical element 12 further comprises suctioning holes 32 dispersed along an exterior surface 14 of the cylindrical element. The suctioning holes can 32 extend from the exterior surface 14 into the one or more suctioning channels 30 and are used to provide an opening into the one or more suctioning channels. According to various embodiments, the handle 20 can comprise a suction regulator device, and a suctioning device or vacuum (not shown) that when activated can generate a pressure sufficient to suction surrounding fluids or other matter from outside the cylindrical element into the suctioning channel 30 via the suctioning holes 32 as can be appreciated.

FIG. 2 illustrates an alternative embodiment of the lighted bougie device 10. The lighted bougie device of FIG. 2 comprises a sleeve 40 that can be attached onto, or over, an existing bougie 12 (or various other medical instruments, such as but not limited to, a dilator, endoscope, sigmoidoscope, colonoscope, rigid proctoscope, ureteroscope, or a hysteroscope). In particular, the sleeve 40 of this particular embodiment can be configured to surround an existing bougie 12, as shown in FIG. 2. In some example embodiments, the sleeve device 40 has fasteners 42 which can be used to attach the sleeve device to an existing bougie 12, as can be appreciated. In depicted embodiments, the fasteners 42 can be clips, but other conventional fasteners, such as snaps, bands, hooks, tape, glue, epoxy, etc. can be used instead.

Figure 2A:
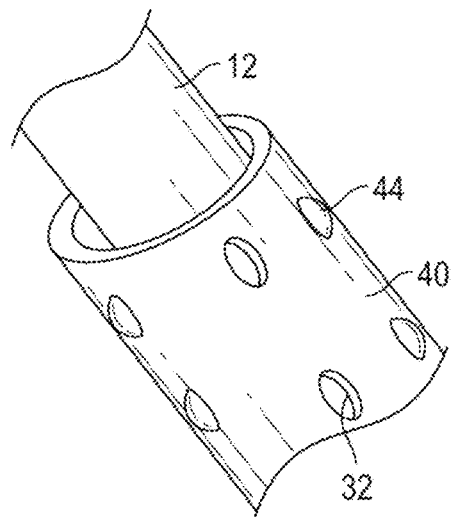
FIG. 2A-2B are close up views of various components of the lighted bougie sleeve device of FIG. 2.
Figure 2B:
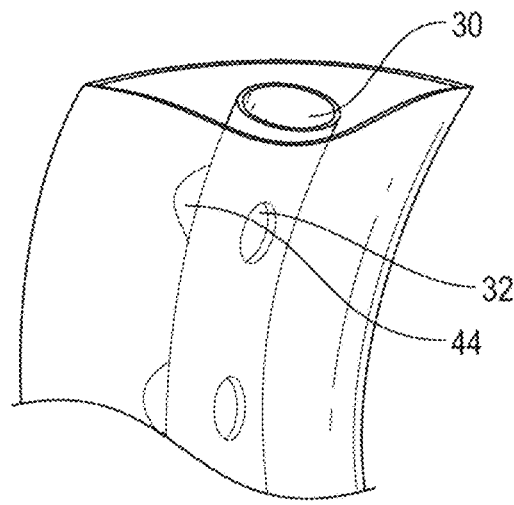

The sleeve device 40, as shown in FIG. 2 (and better seen in FIGS. 2A-2B) comprises one or more LEDs (or other light sources) 44 positioned along an exterior surface and along a length of the sleeve. The LEDs 44 can provide a white light and/or a near-infrared light that can allow visibility of the bougie 12 in the esophagus and/or stomach via a laparoscopic and/or near-infrared camera. In preferred embodiments, as depicted, the sleeve device 40 has a suction channel 30 running along substantially the full length of the sleeve device 40, but the suction channel can also be formed along intermediate lengths of the sleeve device or can be absent from the sleeve as desired. Suctioning holes or ports 32 can disposed along the exterior of the sleeve 15 to provide an ingress into the suctioning channel 30 such that surrounding fluids or other matter from outside the sleeve and bougie can removed through suctioning channel, as can be appreciated.

According to various embodiments, the lighted bougie device 10 can be reusable or disposable and made of permanent or biodegradable material, or near infrared fluorescent polymers. In addition, the lighting system can be battery-powered, The lighted bougie device 10 can be used in various types of surgery including, but not limited to, laparoscopic or robotic surgeries.

According to various embodiments, the standard LSG surgical technique is modified using a near-infrared camera without ICG dye to the standard white light camera on the laparoscope for the purpose of improving the surgeon's ability to detect the exact location of a lighted bougie during a procedure As such, the addition of light in the near-IR spectrum (defined as 700 nm to about 2500 nm) enables far better visualization of a bougie within the stomach. While near-IR light appears in the range of about 700 nm to about 2500 nm, it has been found that the optimal range of near-IR light for use with embodiments according to the present disclosure is about 700 nm to about 1300 nm (and most optimally between 700-850 nm), because a significant portion of this particular range of near-IR light can be transmitted though several centimeters of biological tissue. Alternating between white light and near-IR on the laparoscope will allow the surgeon to clearly visualize both the outside of the stomach and the bougie within it. This dramatic improvement in visualization of the bougie may enable better communication between surgeon and anesthetist during bougie passage through the esophagus and stomach, which may reduce or prevent iatrogenic perforations and reduce or prevent accidental stapling of the bougie during the procedure. Better visualization of the bougie will also enable more accurate sleeve sizing with uniform sleeve diameter regardless of gastric tissue thickness and will allow more accurate removal of excess gastric tissue.

Figure 3A:
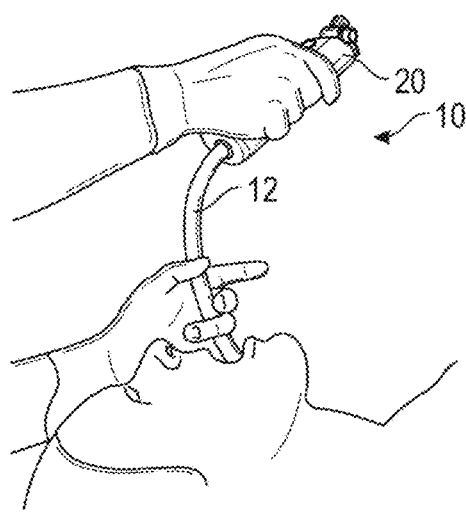
FIGS. 3A-3C are example drawings showing use cases associated with the lighted bougie device and lighted bougie sleeve device of FIGS. 1, 2, and 11 in accordance with various embodiments of the present disclosure.
Figure 3B:
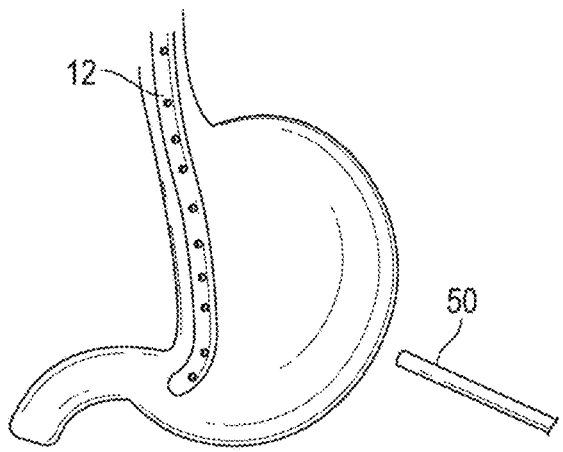
Figure 3C:
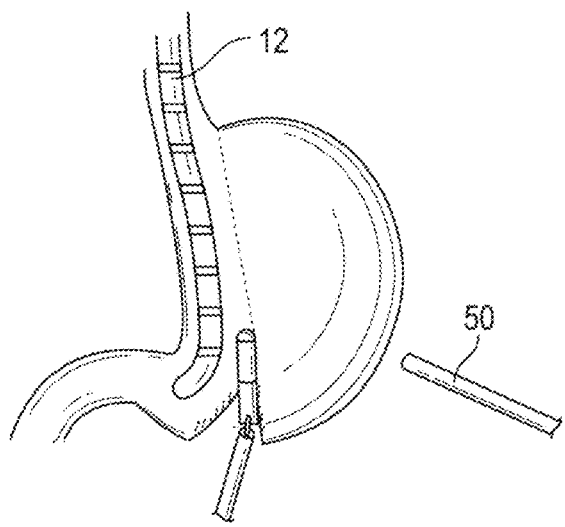

Typical visual cameras, including laparoscopes, are capable of capturing wavelengths of light as seen in the human visual spectrum, referred to as 'white light' images. Near infrared cameras are capable of capturing images with a longer wavelength of light, which is emitted by all objects, referred to as 'near infrared light.' This light is more intense with warmer objects. According to various embodiments of the present disclosure, the use of near infrared light can lead to improved standard surgical techniques. FIGS. 3A-3C illustrate examples of the lighted bougie in use and how the lighted bougie device, when used with a camera with white light and near infrared capabilities, may improve standard surgical techniques. For example, FIG. 3A illustrates the insertion of an illuminated bougie 12 into the esophagus of a patient. FIG. 3B provides an example drawing of the bougie 12 being inserted into the stomach of a patient. A near infrared camera 50 positioned outside the stomach can be used to determine the location of the bougie within the stomach. FIG. 3C illustrates a drawing of an example of the lighted bougie 12 being used as a guide during the construction of the laparoscopic gastric sleeve. In example embodiments, the bougie 12 can be illuminated along its entire length, a portion of its length, or the bougie can be adapted to illuminate all, or a portion of, the operative field in which the bougie is intended to be inserted. As used herein, the operative field is typically defined as a location within a human (or animal) body wherein the surgery is performed and where the anatomical structures/organs that are being operated on are visible.

Figure 4:
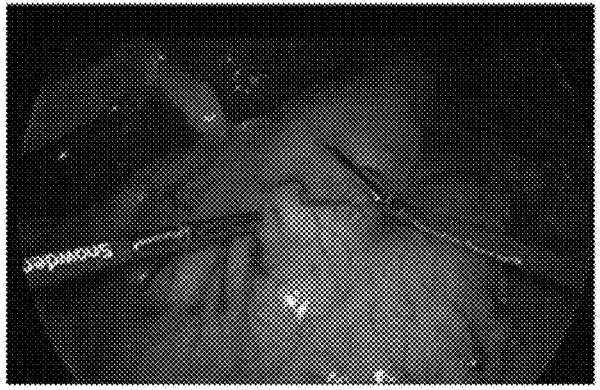
FIGS. 4-6 are example images illustrating the differences in visibility between a white light and a near-infrared light, in accordance with various embodiments of the present disclosure.
Figure 4:
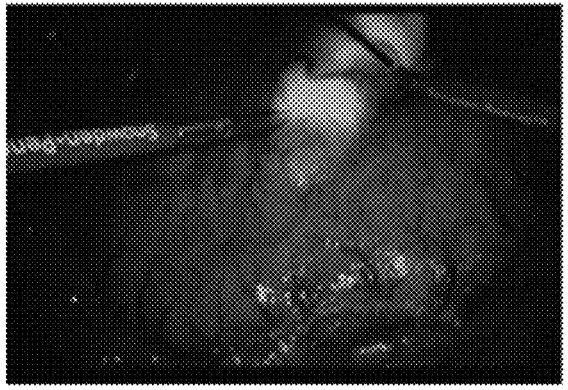
Figure 5:
Figure 5:
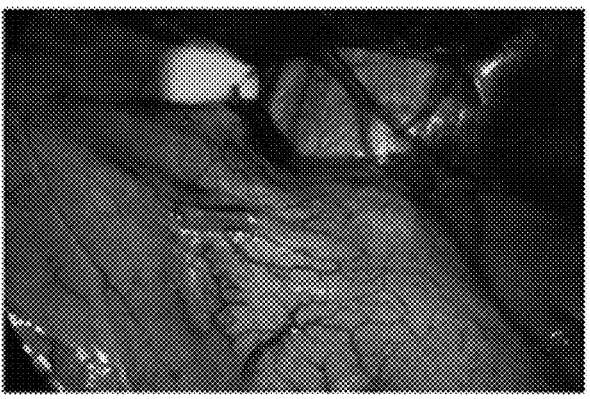

The lighted bougie 12 according to additional example embodiments of the present disclosure can be introduced into the esophagus and stomach with the laparoscope in near-infrared mode, allowing for improved visualization of the bougie by both surgeon and anesthesiologist passing the bougie. FIGS. 4 and 5 illustrate example photos comparing the visibility when using a white light with the visibility provided by the near-infrared camera. As shown in FIGS. 4 and 5, the location of the bougie is more visible when using the near-infrared light and near-infrared camera than when using the white light and standard visual camera.

Figure 6:
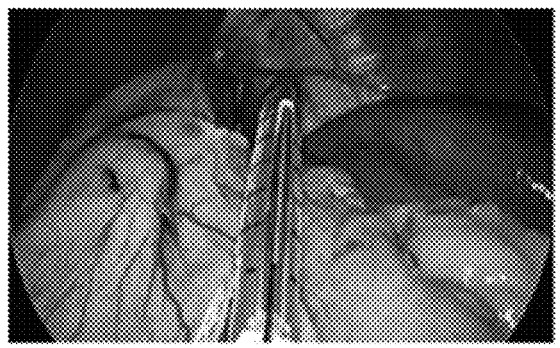
Figure 6:
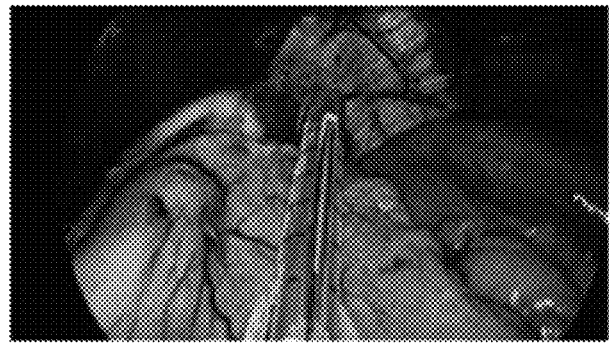

According to the various embodiments of the present disclosure, the LSG can be constructed alternating between the while light view and the near infrared view. The additional near infrared view provides improved visualization of the bougie 12 within the sleeve, allowing for improved and more accurate sleeve sizing, as well as preventing over narrowing of the sleeve at the incisura and at the angle of his. FIG. 6 illustrates example photographs showing the forming of a sleeve with an example lighted bougie 12 in white light and a lighted bougie in near-infrared light. In particular, with the light source on the bougie 12 being in the near IR view, the edge between the bougie and the stomach is more visible.

In laparoscopic or robotic assisted laparoscopic sleeve gastrectomy, the surgeon determines how narrow to make the gastric sleeve. Currently, due to the lack of visibility of the bougie location, a surgeon will often hug the bougie too tight or too loose when creating the sleeve. According to the various embodiments of the present disclosure, the lighted bougie device 12 improves this visibility and can be used as a guide that allows for more consistent, reproducible, standardized gastric sleeve size when the lighted bougie is used with near infrared light while stapling the sleeve. In addition, this similar technique can be used during a gastric bypass operation to form the gastric pouch.

Figure 7:
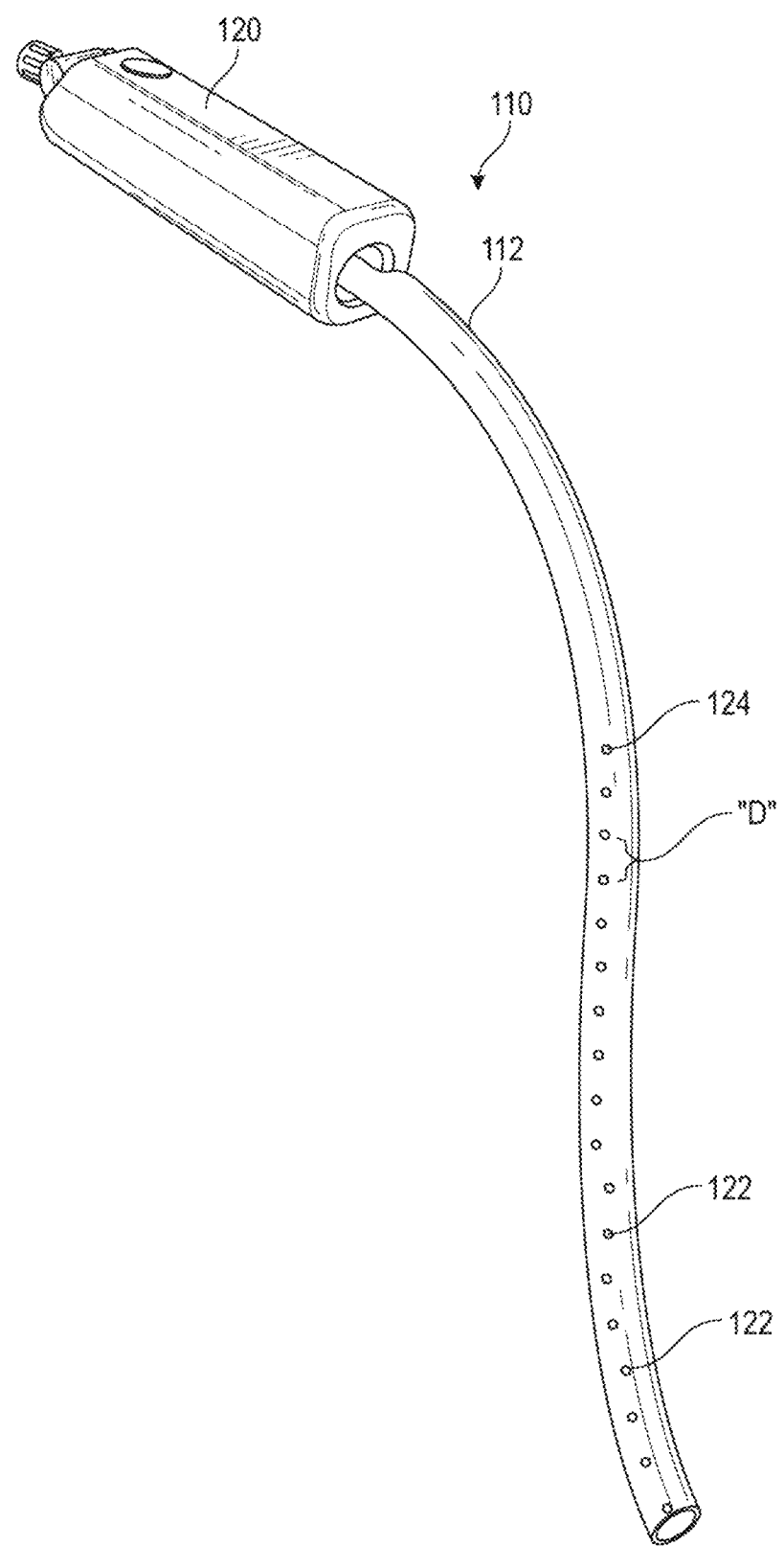
FIG. 7 is a perspective view of a lighted bougie device according to additional example embodiments of the present disclosure.

FIG. 7 depicts additional example embodiments of a lighted bougie device 110 according to the present disclosure. As shown in the drawing figures, the lighted bougie device 110 is constructed similarly to the example lighted bougie device 10 (as described above) and generally includes an elongated cylindrical bougie 112 coupled to a handle 120, and further includes one or more light sources 124. Uniquely, the lighted bougie device 110 as depicted in FIG. 7 includes a plurality of light sources 124 located at measured spaced-apart intervals "D" along the length of bougie 112 (or a portion thereof). As such, the spaced apart light sources 124 allow for intraoperative measurements. In preferred example embodiments the light sources 124 can be LED, fiber optic, or other light sources that are configured to generate white light and/or near-infrared light that can be detected by a white light camera, as well as a near infrared camera. The lights can be different colors, and provide both steady or blinking light. In alternative embodiments, the light sources can be other types of light sources, as can be appreciated by one of ordinary skill. In example configurations, the light sources 124 are spaced apart at intervals "D" of between 0.5 cm and 5 cm. In other example configurations, the light sources are spaced apart at a intervals "D" of approximately 1 cm. In still other example configurations, the light sources are spaced apart at intervals "D" of approximately 2 cms. In still additional example embodiments, the light sources can be spaced apart at other intervals as desired and can vary depending on the levels of precision and accuracy required for any particular application. Thus, the device can be used as a near-infrared guided measuring device.

Presently, surgeons performing laparoscopic and robotic surgeries in the stomach or esophagus have tremendous difficulty in performing intraoperative measurements and typically utilize a string of known length or insert a plastic ruler into the peritoneum, or operative field, to conduct measurements. Embodiments of the lighted bougie device 110 of the present disclosure address the challenge of making intraoperative measurements in laparoscopic or robotic esophagogastric surgeries by including a measuring mechanism within the bougie 112 itself (as disclosed herein). The bougie 112 permits the a surgeon to eliminate the step of introducing a string or ruler into the peritoneal cavity (or operative field), which improves the operative efficiency and reduces the risk of leaving a foreign body in a patient, while still retaining the ability to make the necessary measurements required to complete the surgery.

In practice, when entering the bougie 112 into the peritoneum (or other operative field) the spaced-apart light sources 124 are able to be seen by a surgeon with a white light source/camera in thinner tissues and with a near infrared light source/camera in thicker tissues. By locating the number of visible lights, a surgeon can measure the depth that the bougie 112 has been inserted into the operative field (such as the esophagus, stomach, etc.). For example, the lighted bougie device 110 can be used with a standard white light laparoscopic/robotic camera, or a near infrared laparoscopic/robotic camera. Specifically, for thinner esophagogastric tissues the incremental lights sources 124 of the bougie 112 will be visible with a white light source/camera. For thicker esophagogastric tissues the incremental light sources 124 of the bougie 112 will be visible with use of a near infrared light source/camera.

Figure 8:
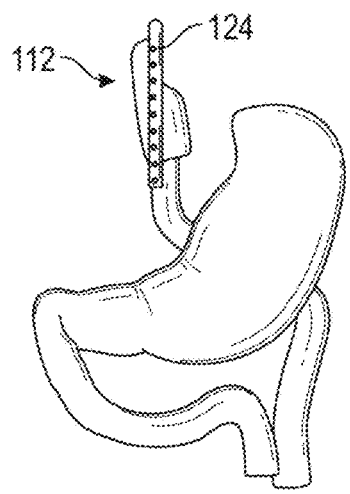
FIGS. 8-10 are example drawings showing use cases associated with the lighted bougie device and lighted bougie sleeve device of FIGS. 1, 2, and 11 in accordance with various embodiments of the present disclosure.
Figure 9:
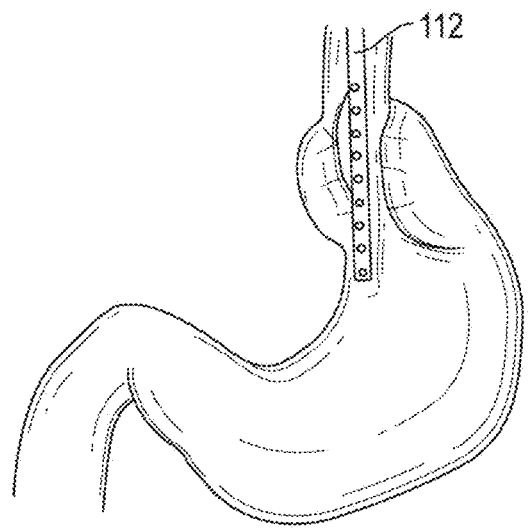
Figure 10:
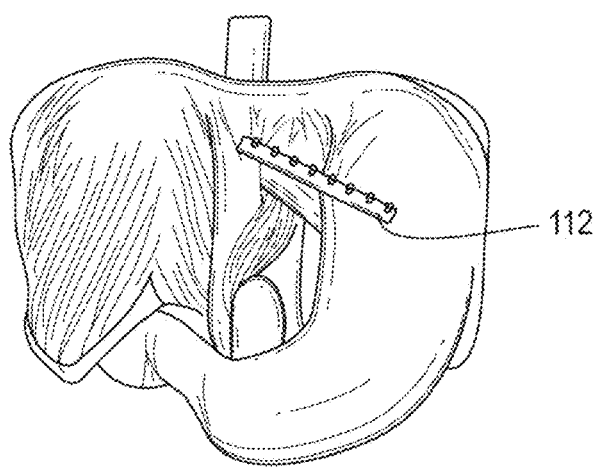

Examples of measurements that can be taken during esophagogastric (foregut) surgeries include, but are not limited to, (1) measurement of the length of a Heller Myotomy during a laparoscopic or robotic Heller operation (FIG. 9); (2) measurement of the distance between the esophageal hiatus and the gastric angle of His during a laparoscopic or robotic hiatal hernia repair (FIG. 10); (3) length of gastric pouch in laparoscopic or robotic bypass surgery (FIG. 8); (4) length of gastric sleeve during a laparoscopic or robotic sleeve gastrectomy; and (5) measurements to localize gastric and lower esophageal tumors during laparoscopic or robotic operations. Additionally, the lighted bougie device 110 can be used to take intraoperative measurements in various other types of surgical procedures, such as, but not limited to, surgeries taking place in the rectum, colon, the upper and lower gastrointestinal tract, urologic organs, and/or gynecological organs.

Figure 11:
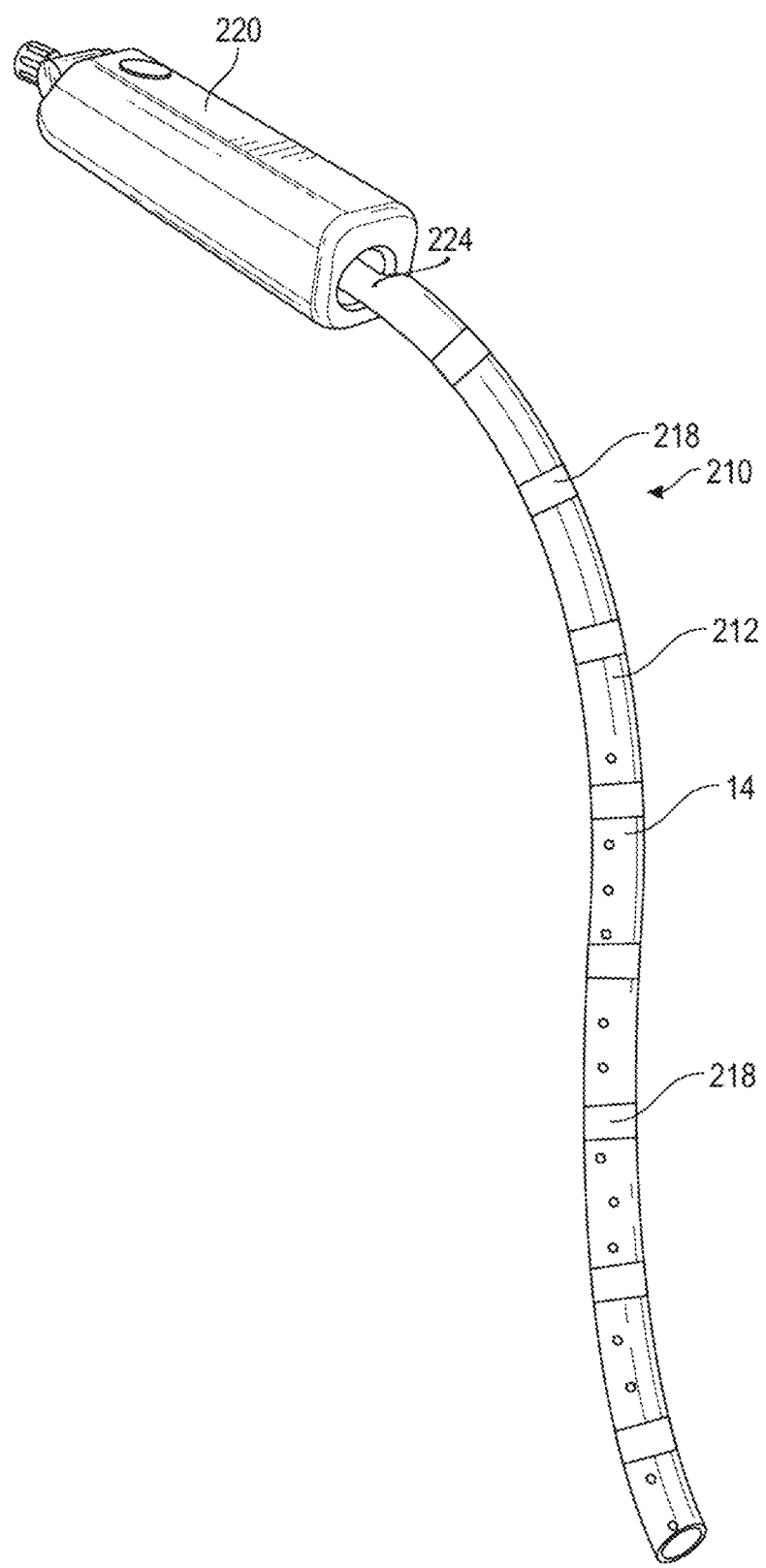
FIG. 11 is a perspective view of a lighted bougie device according to additional example embodiments of the present disclosure.

FIG. 11 illustrates additional example embodiments of the present disclosure. For example, FIG. 11 discloses an example lighted bougie device 210, which generally includes an elongated cylindrical element 212 (e.g., a bougie) that is coupled to a handle 220. The lighted bougie device also includes at least one light source 224 that provides light along a length of the attached bougie 212. In preferred example embodiments, the light is provided along the entire length of the bougie 212, but in other embodiments, the light can be provided along one or more partial sections of the bougie. As seen in FIG. 11, example embodiments can include a single light source 224 for illuminating the bougie 212, or multiple light sources can be used along the length of the bougie as disclosed above with reference to embodiments of the lighted bougie device 110. The light sources 224 can include LED, fiber optic, or other light sources near infrared fluorescent polymers that are configured to generate white light and/or near-infrared light that can be detected by both a white light camera, as well as a near infrared camera.

In this particular embodiment, the lighted bougie device 210 can be used to take intraoperative measurements (of length) by using spaced-apart markings or indicia 218 located along the length of the bougie 212 to designate various lengths and provide visual feedback for a surgeon. In example embodiments, the markings 218 can be formed along the exterior 214 of the bougie 212, the markings can consist of LED lights, or in-between the lights the bougie section can be substantially opaque, in order to block out the underlying light emitted from the light source(s) 224 at the locations the markings appear along the bougie. The markings 218 can be formed within the bougie 212, can be formed from an opaque polymer, or can be formed from other known methods of blocking or reducing light transmission. In still other embodiments, the markings 218 can be numbered, lettered, or otherwise notated to indicate particular lengths of measurement.

In still other example embodiments, the lighted bougie device 210 can be used to measurements of volume. Specifically, the markings 218 formed along the exterior of the bougie 212 can be used to determine a length measurement and the bougie itself will have a known radius, thus an algorithm can be created to calculate a volume of the space the bougie occupies using the equation $V=\pi r^2$. For instance, and by way of example, a user can use the lighted bougie device 210 to calculate the volume of the gastric sleeve and/or gastric pouch during a gastric bypass surgery based on the measured stomach length and bougie radius.

Figure 12:
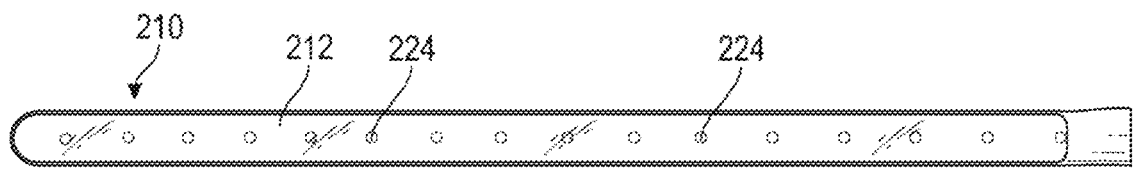
FIG. 12 is a front view of a lighted bougie device according to another example embodiment of the present disclosure.
Figure 13:
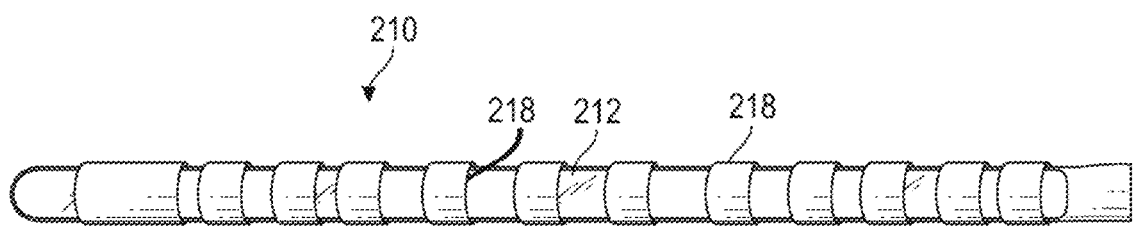
FIG. 13 is a rear view of the lighted bougie device of FIG. 12.

In still other example embodiments, the lighted bougie device 210 can include various light sources 224 along a length of the bougie 212 on a first side of the device (as seen in FIG. 12), and markings 218 on a second side of the device (FIG. 13) to permit measurements with the device.

Various bougies (as depicted in the drawing figures—12, 112, 212—and described throughout this disclosure) can have the following characteristics. The diameter of such bougies can be: 34 French, 36 French, 38 French, 40 French, or otherwise sized as desired. The typical length of an example bougie is 32 inches, the suction hole size is 0.093 inches, the suction hole spacing is approximately 0.5 inches, and the suction hole distance from the distal end of the bougie is approximately 12 inches.

In additional example embodiments, the lighted bougie device of the present disclosure can include a manometric/pressure sensor that measures pressure at the gastroesophageal junction and provides real-time feedback to a surgeon while performing bariatric operations such as gastric sleeve and gastric bypass, or gastroesophageal operations such as hiatal hernia repair or heller myotomy.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A lighted medical device, comprising:
   an elongate member having a proximal end and a distal end;
   at least one light source configured to emit light, the at least one light source coupled to the elongate member such that the light emitted from the at least one light source illuminates at least a portion of the elongate member in a length direction of the elongate member; and
   a plurality of markings disposed along the elongate member, wherein each respective marking in at least a subset of the plurality of markings is located at a corresponding distance in a plurality of distances relative to the proximal or distal end of the elongate member, and each of the plurality of markings is configured to block or reduce transmission of the light emitted from the at least one light source, thereby facilitating one or more intraoperative measurements,
   wherein the at least one light source comprises a plurality of light sources disposed along at least the portion of the elongate member, and
   wherein circumferentially, the plurality of light sources is disposed on one side of the elongate member and the plurality of markings is disposed on another side of the elongate member.

2. The lighted medical device of claim 1, wherein the elongate member is a bougie configured to be inserted into an esophagus or stomach of a patient.

3. The lighted medical device of claim 1, wherein the elongate member is formed with a suction channel, and one or more apertures extending from an exterior surface of the elongate member into the suction channel.

4. The lighted medical device of claim 1, wherein adjacent light sources in the plurality of light sources are spaced apart at intervals of between 0.5 cm and 5 cm.

5. The lighted medical device of claim 1, wherein the at least one light source comprises at least one optic fiber, at least one LED, a polymer containing a near infrared fluorescent material, or any combination thereof.

6. The lighted medical device of claim 1, wherein the light emitted from the at least one light source comprises fluorescent light to guide the one or more intraoperative measurements.

7. The lighted medical device of claim 1, wherein the at least one light source is configured to emit near-infrared light, thereby allowing to locate the elongate member within a patient based on one or more images captured by an image capturing device capable of detecting the near-infrared light.

8. The lighted medical device of claim 7, wherein the at least one light source is further configured to emit white light, thereby allowing to locate the elongate member within a patient based on images captured by an image capturing device capable of detecting the near-infrared light and white light.

9. The lighted medical device of claim 1, wherein each of the plurality of markings is made of an opaque material that blocks or reduces transmission of the light emitted from the at least one light source.

10. The lighted medical device of claim 1, wherein each respective marking in at least the subset of the plurality of markings comprises a notation.

11. The lighted medical device of claim 1, wherein at least one marking in the plurality of markings is disposed circumferentially around the elongate member.

12. The lighted medical device of claim 1, wherein the plurality of markings is formed within the elongate member or disposed on an exterior surface of the elongate member.

13. The lighted medical device of claim 1, wherein the one or more intraoperative measurements comprise a length measurement, a volume measurement, or both.

14. The lighted medical device of claim 1, further comprising:
    a sensor coupled to the elongated member and configured to measure pressure and provide real-time feedback to a surgeon while performing an operation on a patient.

15. The lighted medical device of claim 14, wherein the pressure is measured at a gastroesophageal junction of the patient during a bariatric operation.

16. A lighted medical device, comprising:
    an elongate member having a proximal end and a distal end;
    at least one light source configured to emit light, the at least one light source coupled to the elongate member such that the light emitted from the at least one light source illuminates at least a portion of the elongate member in a length direction of the elongate member; and
    a plurality of markings disposed along the elongate member, wherein each respective marking in at least a subset of the plurality of markings is located at a corresponding distance in a plurality of distances relative to the proximal or distal end of the elongate member, and each of the plurality of markings is configured to block or reduce transmission of the light emitted from the at least one light source, thereby facilitating one or more intraoperative measurements,
    wherein a distance separating adjacent markings disposed on a proximal or distal end portion of the elongate member is less than a distance separating adjacent markings disposed on a middle portion of the elongate member.

17. The lighted medical device of claim 16, wherein:
    a marking in the plurality of markings has a width in the length direction of the elongate member;
    the distance separating adjacent markings disposed on the proximal or distal end portion of the elongate member is less than the width of the marking in the plurality of markings; and
    the distance separating adjacent markings disposed on the middle portion of the elongate member is equal to or greater than the width of the marking.

18. The lighted medical device of claim 1, wherein each of the plurality of markings has a width in the length direction of the elongate member that is at least 0.5 times, at least 0.6 times, at least 0.7 times or at least 0.8 times a diameter of the elongate member.

19. A lighted medical device, comprising:
    an elongate member having a proximal end and a distal end;
    at least one light source configured to emit light, the at least one light source coupled to the elongate member such that the light emitted from the at least one light source illuminates at least a portion of the elongate member in a length direction of the elongate member; and
    a plurality of markings disposed along the elongate member, wherein each respective marking in at least a subset of the plurality of markings is located at a corresponding distance in a plurality of distances relative to the proximal or distal end of the elongate member, and each of the plurality of markings is configured to block or reduce transmission of the light emitted from the at least one light source, thereby facilitating one or more intraoperative measurements,
    wherein at least one marking in the plurality of markings is disposed on the elongate member at a distance to the proximal end of the elongate member that is less than 4 times, less than 3 times, less than 2.5 times or less than 2 times a diameter of the elongate member.

20. A method, comprising:
    inserting at least a proximal portion of the elongate member of the lighted medical device of claim 1 into a hollow organ of a patient;
    illuminating an operative field with the light emitted from the at least one light source of the lighted device;
    determining a location of the elongate member within the patient based on one or more images captured from an image capturing device; and
    measuring one or more of the following:
        a length of a Heller Myotomy during a laparoscopic or robotic Heller operation;
        a distance between an esophageal hiatus and a gastric angle of His during a laparoscopic or robotic hiatal hernia repair;
        a length of a gastric pouch in laparoscopic or robotic bypass surgery;
        a length of gastric sleeve during a laparoscopic or robotic sleeve gastrectomy; and
        localize gastric and lower esophageal tumors and measure resection margins for said tumors during laparoscopic or robotic operations.

21. The method of claim 20, wherein the light emitted from the at least one light source comprises fluorescent light to guide the one or more intraoperative measurements.

* * * * *